(12) United States Patent
Tanojo et al.

(10) Patent No.: US 7,300,649 B2
(45) Date of Patent: Nov. 27, 2007

(54) COSMETIC AND COSMECEUTICAL COMPOSITIONS FOR RESTORATION OF SKIN BARRIER FUNCTION

(75) Inventors: Hanafi Tanojo, Palo Alto, CA (US); Xinfan Huang, Menlo Park, CA (US)

(73) Assignee: GenePharm, Inc., Sunnyvale, CA (US)

( * ) Notice: Subject to any disclaimer, the term of this patent is extended or adjusted under 35 U.S.C. 154(b) by 9 days.

(21) Appl. No.: 11/275,994

(22) Filed: Feb. 8, 2006

(65) Prior Publication Data

US 2006/0182770 A1 Aug. 17, 2006

Related U.S. Application Data

(60) Provisional application No. 60/652,196, filed on Feb. 11, 2005.

(51) Int. Cl.
*A61K 31/74* (2006.01)
*A61K 33/14* (2006.01)

(52) U.S. Cl. .................... 424/78.03; 424/678; 424/681

(58) Field of Classification Search ............. 424/78.03, 424/678, 681
See application file for complete search history.

(56) References Cited

U.S. PATENT DOCUMENTS

| | | | |
|---|---|---|---|
| 4,139,619 A | 2/1979 | Chidsey | |
| 4,596,812 A | 6/1986 | Chidsey et al. | |
| 4,943,432 A | 7/1990 | Biener | |
| 5,082,489 A * | 1/1992 | Watson et al. | 504/117 |
| 5,391,538 A * | 2/1995 | Heiny et al. | 504/117 |
| 5,653,970 A * | 8/1997 | Vermeer | 424/70.24 |
| 5,955,067 A * | 9/1999 | Oge et al. | 424/78.07 |
| 6,403,530 B1 * | 6/2002 | Sands et al. | 504/116.1 |
| 2006/0084574 A1 * | 4/2006 | Bailey et al. | 504/117 |

FOREIGN PATENT DOCUMENTS

| | | |
|---|---|---|
| EP | 0524109 B1 | 6/1995 |
| EP | 0737471 A2 | 10/1996 |
| EP | 0761204 B1 | 4/1998 |
| EP | 0852949 A2 | 7/1998 |
| EP | 0680749 B1 | 9/1998 |
| EP | 0895779 A1 | 2/1999 |

(Continued)

OTHER PUBLICATIONS

Baird et al., Phoma macrostoma Causing Leaf Spot on Fevertree, 1993, Plant Dis. 77: 1168.*

(Continued)

*Primary Examiner*—Johann R. Richter
*Assistant Examiner*—Nikki Handy
(74) *Attorney, Agent, or Firm*—Wilson Sonsini Goodrich & Rosati (57) ABSTRACT

Compositions, kits and methods are provided for restoring skin barrier function to skin exposed to environmental elements and/or in a pathological condition. In general, divalent cations such as calcium ions and/or magnesium ions are included in a physiologically acceptable medium. In some embodiments, divalent cations are balanced with monovalent cations such as sodium and potassium ions at appropriate ratios in order to maintain the homeostasis of skin barrier. The compositions, kits and methods can be used as cosmetics, cosmeceuticals or pharmaceuticals for improving skin condition, and preventing or treating dermatological diseases and skin disorders.

39 Claims, 3 Drawing Sheets

FOREIGN PATENT DOCUMENTS

| | | |
|---|---|---|
| EP | 0765668 B1 | 3/1999 |
| EP | 0906752 A1 | 4/1999 |
| EP | 0909556 A1 | 4/1999 |
| EP | 0925779 A1 | 6/1999 |
| EP | 1038519 A1 | 9/2000 |
| EP | 0764444 B1 | 3/2002 |
| EP | 0892642 B1 | 8/2002 |
| FR | 2642968 | 8/1990 |
| WO | WO 93/18743 A1 | 9/1993 |
| WO | WO 96/09048 A1 | 3/1996 |
| WO | WO 96/36165 A1 | 11/1996 |
| WO | WO 99/10318 | 3/1999 |
| WO | WO 99/22707 A1 | 5/1999 |
| WO | WO 99/32077 A1 | 7/1999 |

OTHER PUBLICATIONS

Carafoli, et al. The Calcium Signal. Sci. Am. 1985; 253:70-78.

Clapham, D. E. Calcium signaling. Cell. 1995; 80:259-268.

Denda, et al. Influx of calcium and chloride ions into epidermal keratino-cytes regulates exocytosis of epidermal lamellar bodies and skin permeability barrier homeostasis. J. Invest. Dermatol. 2003; 121:362-367.

Denda, et al. Some magnesium salts and a mixture of magnesium and calcium salts accelerate skin barrier recovery. Arch Dematol Res. 1999; 291:560-563.

Denda, et al. Stratum corneum lipid morphology and transepidermal water loss in normal skin and surfactant-induced scaly skin. Arch. Dermatol. Res. 1994; 286:41-46.

Elias, et al. Normal mechanisms and pathophysiology of epidermal permeability barrier homeostasis. Curr. Opin. Dermatol. 1993; 231-237.

Forslind, et al. Human skin physiology studied by particle probe microanalysis. Scanning Microsc. 1995; 9:1011-1026.

Kirk-Othmer. Encyclopedia of Chemical Technology. 1979. 3rd Ed. vol. 22: pp. 333-432. John Wiley & Sons. in particular pp. 347-377.

Lee, et al. An update of the defensive barrier function of skin. Yonsei Med J. 2006; 47(3):293-306.

Lee, et al. Calcium and potassium are important regulators of barrier homeostasis in murine epidermis. J. Clin. Invest. 1992; 89:530-538.

Malmqvist, et al. The use of PIXE in experimental studies of the physiology of human skin epidermis. Biol. Trace Elem.Res. 1987; 12:297-308.

Mao-Qiang, et al. Calcium and potassium inhibit barrier recovery after disruption, independent of the type of insult in hairless mice. Exp. Dermatol. 1997; 6:36-40.

Matz, et al. Balneotherapy in dermatology. Dermatol Ther. 2003; 16(2):132-40.

Menon, et al. Selective Obliteration of the Epidermal Calcium Gradient Leads to Enhanced Lamellar Body Secretion. J. Invest. Dermatol. 1985; 102:789-795.

Menon, et al. Ultrastructural localization of calcium in psoriatic and normal human epidermis. Arch. Dermatol. 1991; 127:57-63.

Momose, et al. Calcium ions are abnormally distributed in the skin of haemodialysis patients with uraemic pruritus. Nephrol Dial Transplant. 2004; 19(8):2061-6.

Pallon, et al. Pixe analysis of pathological skin with special reference to psoriasis and atopic dry skin. Cell Mol Biol (Noisy-legrand). 1996; 42 (1):111-8.

Potts, et al. The influence of stratum corneum morphology on water permeability. J. Invest. Dermatol. 1991; 96:495-499.

Proksch, et al. Bathing in a magnesium-rich Dead Sea salt solution improves skin barrier function, enhances skin hydration, and reduces inflammation in atopic dry skin. Int J Dermatol. 2005; 44(2):151-7.

Shani, et al. Penetration of selected Dead Sea minerals through a healthy rabbit skin, from a sustained-release transparent varnish, as a prospective treatment for psoriasis. Journal of the European Academy of Dermatology & Venereology. 1995; 4(3):267-272.

Shani, et al. Skin penetration of minerals in psoriatics and guineapigs bathing in hypertonic salt solutions. Pharmacol Res Commun. 1985; 17(6):501-12.

Tanojo, et al. Role of calcium ions in relation to skin barrier function. In Percutaneous Absorption, 3$^{rd}$ Ed., Bronaugh & Maibach, ed., Marcel Dekker, NY. 1999; pp. 939-950.

Tanojo, et al. Role of calcium ions in the regulation of skin barrier homeostasis. Dry skin and moisturizers. 2nd Ed. CRC Press. Taylor & Franncis Group. Boca Raton, FL. 2006; pp. 63-70.

Yoshizawa, et al. Sea water or its components alter experimental irritant dermatitis in man. Skin Res Technol. 2001; 7(1):36-9.

* cited by examiner

COSMETIC AND COSMECEUTICAL COMPOSITIONS FOR RESTORATION OF SKIN BARRIER FUNCTION

CROSS REFERENCE

This application claims the benefit of U.S. Provisional Application No. 60/652,196, filed Feb. 11, 2005, which is incorporated herein by reference in its entirety.

BACKGROUND OF THE INVENTION

The skin serves numerous functions but its primary function is as a protective layer or barrier. The most important role of the skin for terrestrial animals is to protect the water-rich internal organs from the dry environment. This cutaneous barrier function of the skin resides in the upper most thin layer (approximately 10-20 µm in humans) called stratum corneum. The water impermeability of this layer is 1000 times-high than that of other membranes of living organisms. Potts & Francoeur (1991) J. Invest. Dermatol. 96;495-499.

The stratum corneum is composed of two components, i.e., protein-rich nonviable cells and intercellular lipid domains. Elias et al. (1993) Curr. Opin. Dermatol. 231-237. The lipid molecule in the intercellular domain form a bilayer structure. The water impermeability is due to the conformation of the lipid molecules and also the order of the deal cells. Denda et al. (1994) Arch. Dermatol. Res. 286:41-46. Because of this specific "brick and mortar" structure, the stratum corneum shows high water impermeability.

The uppermost layer of the skin, called epidermis, is mainly constructed of keratinocytes. The epidermis is in a constant state of self-replacement. At the bottom layer, keratinocyte stem cells divide into daughter cells, which are displaced outward, and which differentiate through successive overlying layers to enter the stratum corneum. Then, the keratinocytes die (apoptosis) and their cellular organella and cytoplasm disappear during the final process of differentiation. Intercellular lipids are primarily generated from exocytosis of lipid-containing granules called lamellar bodies, during the terminal differentiation. The secreted lipids spread over the intercellular domains and form a bilayer structure. Elias et al. (1993), supra.

Ionic signals play important role in the homestatic mechanim of the epidermal barrier function. Lee et al. (1992) J. Clin. Invest. 89:530-538. In normal skin, calcium is localized with high concentration in the epidermal granular layer, i.e., the uppermost layer of the epidermis, just below the stratum corneum. On the contrary, the concentration potassium is the highest in the spinous layer, i.e., middle of the epidermis, and the lowest in the granular layer.

Calcium is a universal messenger, even in simple organisms and plants. The combination of its ionic radius and double charge may allow it tighter binding to receptors to the exclusion of other ions such as magnesium, leading to strong, specific binding. Carafoli & Penniston (1985) The Calcium Signal. Sci. Am. 253:70-78. The specificity enables cells to form special receptors to assess signals from calcium. For many parts of the body, $Ca^{2+}$ often acts as a second messenger in a manner similar to cAMP. In skin, calcium can provide signals for the cells, either extracellular or intracellular (in the cytosol). The extra- and intracellular signaling may be connected to each other, but may also act separately. It has been found that intracellular $Ca^{2+}$ increases with raised extracellular $Ca^{2+}$. This implies that increased intracellular $Ca^{2+}$ is the actual signal to trigger keratinocytes differentiation. Tanojo & Maibach (1999) in Percutaneous Absorption, $3^{rd}$ Ed., Bronaugh & Maibach, ed., Marcel Dekker, NY, pp. 939-950.

As $Ca^{2+}$ cannot be metabolized like other second-messenger molecules, cells tightly regulate intracelular levels thorough numerous binding and specialized extrusion proteins. Clapham (1995) Cell 80:259-268. The concentration of calcium in extracellular spaces (generally ~1.5 mM) is four orders of magnitude higher than in the cytosol (~0.1 µM). In excitable cells, for example, muscle cells, the extracellular concentration of calcium must be closely regulated to keep it at its normal level of ~1.5 mM, so that it cannot accidentally trigger the muscle contraction, the transmission of nerve impulses, and blood clotting. In other cells, including keratinocytes, the extracellular level is maintained in a specific equilibrium with the intracellular concentrations.

As described above, there is a high calcium gradient between extra- and intracellular domains of keratinocytes, which requires tight regulation. Moreover, a calcium gradient is present within the epidermis, with higher quantities of $Ca^{2+}$ in the upper than the lower epidermis. Menon et al. (1985) J. Invest. Dermatol. 102:789-795. $Ca^{2+}$ concentration increases steadily from the basal region to stratum corneum, which this is not the case with other ions. Forslind et al (1995) Scanning Microsc. 9:1011-1026. Such a gradient is not observed in skin abnormalities related to the formation of abnormal barrier function, such as psoriasis. Menon & Elias (1991) Arch. Dermatol. 127:57-63. It has been reported that disruption of the skin barrier with acetone treatment or tape stripping depletes $Ca^{2+}$ from the upper epidermis, resulting in the loss of the $Ca^{2+}$ gradient. This is due to accelerated water transit that leads to the increased passive loss of $Ca^{2+}$ into and through the stratum corneum. Mao-Qiang et al. (1997) Exp. Dermatol. 6:36-40.

In summary, calcium ions play an important role in the homeostasis of skin barrier. A change in the barrier will change the calcium ion gradient in skin and lead to barrier repair process. A severe change might lead to a high degree of calcium signaling, which may induce the activation of various processes, from increased synthesis of skin components or messengers to the inflammatory reactions. Thus, there exists a need for compositions and methods for activating the barrier repair process to restore normal barrier function to skin adversely affected by environmental elements or pathological conditions.

SUMMARY OF THE INVENTION

Compositions, kits and methods are provided for restoring skin barrier function to skin exposed to environmental elements and/or in a pathological condition. In general, divalent cations such as calcium ions and/or magnesium ions are included in a physiologically acceptable medium. In some embodiments, divalent cations are balanced with monovalent cations such as sodium and potassium ions at appropriate ratios in order to maintain the homeostasis of skin barrier. The compositions, kits and methods can be used as cosmetics, cosmeceuticals or pharmaceuticals for improving skin condition, and preventing or treating dermatological diseases and skin disorders.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

DETAILED DESCRIPTION OF THE INVENTION

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

The present invention provides innovative compositions and methods for restoring skin barrier function. The invention is based on fundamental understanding of the roles calcium ions play in the regulation of skin barrier function and the intricate balance between monovalent and divalent ions for maintaining the homeostasis of skin barrier.

It is known that the limited amount of calcium in skin compared to sodium, potassium and magnesium enables the skin cells to monitor the high and low level accurately. However, the inventors believe that applying the calcium ions alone to the skin may not only be useless, but can also be harmful, because in monitoring the calcium, the skin also takes into account the presence of other ions. In the case of high calcium only application, the skin will take it as overdosing and trigger negative feedback in response which may cause unpredictable adverse effects. Hence, the inventors believe that the application of divalent ions such as calcium or magnesium ions must be balanced with other components to restore or enhance skin barrier function.

According to the present invention, the compositions and methods are provided for skin care, including prevention or treatment of abnormal skin conditions due to compromised skin barrier function, such as dehydration and inflammation. Without being bound to the particular theory or mechanism of action, the compositions are believed to exert their beneficial effects to the skin through: i) maintaining the balance of major ions in skin, especially between monovalent and divalent cations; ii) restoring the balance of the major ions in skin, especially between monovalent and divalent cations; and iii) restoring and maintaining the growth process of skin cells, which is influenced by the ion balance.

By restoring the balance of major ions in the skin, various beneficial effects can be achieved. As skin receives various challenges from the environment and changes in diet, it tries to adapt by adjusting the quality of skin barrier. When the environment becomes dry, the skin may create stiff barrier to prevent high level of water loss. The stiff barrier can later result in rough and dull skin. Interestingly, skin uses the calcium ions to indirectly monitor the dryness of the environment. If the dryness is exaggerated by other cause, like skin diseases or secondary insults/challenges, the ion balance will be shifted for a long time, triggering the continuous formation of poor quality barrier function. Hence, the restoration of ion balance will induce the regeneration of normal skin barrier layer, which has the optimum barrier function. The formation of a normal skin barrier can also ensure the healthy growth of other cells and components of the skin, such as lymphocytes and keratinocytes, thereby achieving optimum skin conditions.

In one aspect of the invention, a composition for skin care is provided. In one embodiment the composition comprises about 0.01-8% w/w divalent calcium ion and/or divalent magnesium ion based on the total weight of the composition in a physiologically acceptable medium. Optionally, the ratio of divalent calcium ion to divalent magnesium ion ranges from 5:1 to 1:5, from 3:1 to 1:3, from 2:1 to 1:2, or from 3:2 to 2:3. The physiologically acceptable medium is preferably a cosmetically or pharmaceutically acceptable carrier. Preferably, calcium ions are provided in the form of calcium chloride; and magnesium ions are provided in the form of magnesium chloride.

In another embodiment, the composition comprises divalent calcium ion and monovalent ion at a ratio of 15:1 to 1:20 in a physiologically acceptable medium, wherein the amount of the divalent calcium ion is about 0.01-8% by weight relative to the total weight of the composition. Optionally, the ration of divalent calcium ion to monovalent ion ranges from 8:1 to 1:10, from 6:1 to 1:3, from 4:1 to 1:5, from 2:1 to 1:3, or from 1:1 to 1:2. Preferably, the monovalent ions are sodium or potassium ions in a form of sodium chloride, potassium chloride or potassium bromide.

According these embodiments, in the compositions divalent cations (e.g., calcium or magnesium cations) are combined with monovalent cations (e.g., sodium or potassium cations) at a proper ratio in order to maintain the balance of ions in skin barrier and avoid triggering negative back in response. The divalent cations can also be combined with other major skin components as cholesterol, fatty acids and amino acids or their equivalents.

In a particular embodiment, the divalent calcium or magnesium ion are preferably combined with monovalent sodium and potassium ion in an aqueous liquid medium. The aqueous liquid medium constitutes an aqueous phase, which may be the continuous phase of the composition.

The aqueous phase may consist essentially of water; it may also comprise a mixture of water and of water-miscible solvent (miscibility in water of greater than 50% by weight at 25° C.), for instance lower monoalcohols containing from 1 to 5 carbon atoms such as ethanol or isopropanol, glycols containing from 2 to 8 carbon atoms, such as propylene glycol, ethylene glycol, 1,3-butylene glycol or dipropylene glycol, $C_3$-$C_4$ ketones and $C_2$-$C_4$ aldehydes, and glycerin.

The aqueous phase (water and optionally the water-miscible organic solvent) may be present in a content ranging from 1% to 98% by weight, relative to the total weight of the composition, optionally from 3% to 96%, from 40% to 95%, from 50% to 90%, from 60% to 90%, or from 70% to 85%.

In the aqueous liquid formulation, the amount of divalent calcium ion is preferably about 0.1-8%, optionally about 0.5-5%, or optionally about 1-3%. The divalent calcium ion is preferably provided by adding $CaCl_2$ to the aqueous phase.

Such an aqueous formulation can be used as skin toner, moisturizer or humectant to promote skin barrier repair and restore normal skin barrier function to skin exposed to or damaged by environmental elements or in pathological conditions.

Optionally, the composition of the present invention is in a form of emulsion or cream formulation. It can contain emulsifying surfactants, present in particular in a proportion ranging from 2% to 30% by weight relative to the total weight of the composition, and better still from 5% to 15%. These surfactants may be chosen from anionic and nonionic surfactants. Reference may be made to the document "Encyclopedia of Chemical Technology, Kirk-Othmer", volume 22, pp. 333-432, 3rd edition, 1979, Wiley, for the definition of the properties and functions (emulsifying) of surfactants, in particular pp. 347-377 of said reference, for the anionic and nonionic surfactants.

The surfactants preferably used in the composition according to the invention are chosen from: nonionic surfactants: fatty acids, fatty alcohols, polyethoxylated or polyglycerolated fatty alcohols such as polyethoxylated stearyl or cetylstearyl alcohol, fatty acid esters of sucrose, alkylglucose esters, in particular polyoxyethylenated fatty esters of $C_1$-$C_6$ alkyl glucose, and mixtures thereof; anionic surfactants: $C_{16}$-$C_{30}$ fatty acids neutralized with amines, aqueous ammonia or alkaline salts, and mixtures thereof. Surfactants which make it possible to obtain an oil-in-water or wax-in-water emulsion are preferably used.

In the cream formulation, the amount of divalent calcium ion is preferably about 0.01-8%, optionally about 0.05-0.5%, or optionally about 0.1-0.3%. The divalent calcium ion is preferably provided by adding $CaCl_2$ to the emulsion.

Optionally, the composition of the present invention is in a form of aqueous gel or hydrogel formulation. The hydrogel formulation comprises a thickening agent to thicken the liquid solution. Examples of the thickening agents include, but are not limited to, carbomers, cellulose base materials, gums, algin, agar, pectins, carrageenan, gelatin, mineral or modified mineral thickeners, polyethylene glycol and polyalcohols, polyacrylamide and other polymeric thickeners. The thickening agents which give the stability and optimal flow characteristics of the composition are preferably used.

In the hydrogel formulation, the amount of divalent calcium ion is preferably about 0.01-8%, optionally about 0.05-0.5%, or optionally about 0.1-0.3%. The divalent calcium ion is preferably provided by adding $CaCl_2$ to the formulation.

The compositions according to the invention may further comprise an effective amount of a physiologically acceptable antioxidant selected from the group consisting of butylated p-cresol, butylated hydroquinone monomethyl ether, and a tocopherol. The antioxidant can be present in amounts of 0.005-5% by weight of the total composition.

The compositions according to the invention may further comprise natural or modified amino acid, such as arginine, cystine, glutamine, histidine, isoleusine, leucine, lysine, methionine, phenylalanine, threonine, tryptophan, tyrosine, and valine. The amino acid can be present in amounts of from 0.002-6% by weight of the total composition.

The compositions according to the invention may further comprise natural or modified sterol compound such as cholesterol and plant sterol (also called phytosterol) such as stigmasterol, campesterol, β-sitosterol, chalinosterol, clionasterol, brassicasterol, α-spinasterol, dancosterol, desmosterol, and poriferasterol. The amino acid can be present in amounts of from 0.001-5% by weight of the total composition.

The compositions according to the invention may further comprise natural or modified collagen, silk protein or soy protein. The protein can be present in amounts of from 0.01-10% by weight of the total composition.

The compositions according to the invention are preferably formulated for topical application to keratin materials such as the skin, the hair, the eyelashes or the nails. They may be in any presentation form normally used for this type of application, especially in the form of an aqueous or oily solution, an oil-in-water or water-in-oil emulsion, a silicone emulsion, a microemulsion or nanoemulsion, an aqueous or oily gel or a liquid, pasty or solid anhydrous product.

The inventive compositions may be more or less fluid and may have the appearance of a white or colored cream, an ointment, a milk, a lotion, a serum, a paste, a mousse or a gel. They may optionally be topically applied onto the skin in the form of an aerosol, a patch or a powder. They may also be in solid form, for example, in the form of a stick. They may be used as care products and/or as makeup products for the skin. Alternatively, they may be formulated as shampoos or conditioners.

In known fashion, the compositions of the invention may also contain additives and adjuvants that are common in cosmetics, such as hydrophilic or lipophilic gelling agents, preservatives, antioxidants, solvents, fragrances, fillers, pigments, odor absorbers and dyestuffs. The amounts of these various additives and adjuvants are those conventionally employed in the field under consideration, and range, for example, from 0.01% to 20% of the total weight of the composition. Depending on their nature, these additives and adjuvants may be introduced into the fatty phase or into the aqueous phase.

When the composition according to the invention is an emulsion, the proportion of the fatty phase advantageously ranges from 2% to 80% by weight and preferably from 5% to 50% by weight relative to the total weight of the composition. The fatty substances, emulsifiers and co-emulsifiers included in the composition in emulsion form are selected from among those conventionally formulated in the field under consideration. The emulsifier and co-emulsifier are preferably present in the composition in a proportion ranging from 0.3% to 30% by weight and preferably from 0.5% to 20% by weight relative to the total weight of the composition.

Exemplary fatty substances according to the invention include the oils and especially mineral oils (liquid petroleum jelly), oils of plant origin (avocado oil, evening primrose oil, safflower oil, soybean oil, wheat germ oil, apricot kernel oil), oils of animal origin (lanolin), synthetic oils (perhydrosqualene), silicone oils (cyclomethicone) and fluoro oils (perfluoro polyethers). Fatty alcohols such as cetyl alcohol, fatty acids, waxes and gums and in particular silicone gums are also representative fatty substances.

Exemplary emulsifiers and co-emulsifiers according to the invention include fatty acid esters of polyethylene glycol, such as PEG-100 stearate, PEG-50 stearate and PEG-40 stearate; fatty acid esters of polyols, such as glyceryl stearate, sorbitan tristearate and oxyethylenated sorbitan stearates commercially available under the trademark Tween™20 or Tween™60, for example; and mixtures thereof.

And exemplary hydrophilic gelling agents include in particular, carboxyvinyl polymers (carbomer), acrylic copolymers such as acrylate/alkyl acrylate copolymers, polyacrylamides, polysaccharides, natural gums and clays. Exemplary lipophilic gelling agents include, in particular, modified clays, for example bentones, metal salts of fatty acids and hydrophobic silica.

The present invention also features a cosmetic regime/regimen for skin care by topical application thereon of a composition containing, formulated into a physiologically acceptable medium (vehicle, diluent or carrier), 0.01-15% w/w divalent calcium ion, either alone or in combination with at least one other compound as described above.

This invention relates more particularly to a cosmetic regime or regimen for treating the adverse signs of aging of the skin and/or a dull complexion and/or skin or hair pigmentation disorders and/or skin dryness and/or hyperseborrhoea and/or hyperseborrhoea-related imperfections and/or sensitive skin and/or dandruff and/or natural hair loss and/or baldness, comprising the topical application onto the skin or the hair, for such period of time as required to elicit the desired cosmetic/therapeutic response, of a composition containing, formulated into a physiologically acceptable medium, 0.01-15% w/w divalent calcium ion, either alone or in combination with at least one other compound as described above.

By the expression "signs of aging of the skin" are intended wrinkles and fine lines, loss of firmness and/or elasticity of the skin, cutaneous atrophy, a more irregular skin grain with presence of dilated pores, loss of radiance of the skin and/or pigmentary marks.

By the expression "sensitive skin" is intended skin that has been characterized in EP-0,680,749 B1, hereby incorporated by reference. It has thus been shown that the symptoms associated with sensitive skin included more or less painful sensations experienced in an area of skin, such as stinging, tingling, itching or pruritus, burning, redness, hotness, discomfort, tautness, etc. These symptoms may be manifested in response to various factors such as, inter alia, sweat, friction, the emotions, foods, the wind, shaving, soap, surfactants, hard water with a high calcium concentration, temperature variations or wool.

Thus invention also features cosmetic compositions containing, in a physiologically acceptable medium therefor (vehicle, diluent or carrier), 0.01-15% w/w divalent calcium ion, and at least one other active agent compound selected from among: a desquamating agent, a moisturizer, a depigmenting or propigmenting agent, an anti-glycation agent, an NO-synthase inhibitor, a 5α-reductase inhibitor, a lysyl and/or prolyl hydroxylase inhibitor, an agent for stimulating the synthesis of dermal or epidermal macromolecules and/or for preventing their degradation, an agent for stimulating the proliferation of fibroblasts and keratinocytes and/or keratinocyte differentiation, a muscle relaxant, a compound for reducing irritation, an antimicrobial agent, a tensioning agent, an anti-pollution agent or a free-radical scavenger.

The present invention also features cosmetic compositions containing, in a physiologically acceptable medium, 0.01-15% w/w divalent calcium ion, and at least one UV-screening agent selected from among certain UVA and/or UVB screening agents and/or at least one optionally coated inorganic pigment.

The compositions according to the invention are well suited for topical application onto keratin substrates/materials such as the skin, keratin fibers (head hairs and eyelashes) and the nails.

By the expression "physiologically acceptable medium" is intended a medium that is compatible with the skin and/or its integuments.

Various compounds that may be formulated into the compositions according to the invention will now be more fully described.

1. Desquamating Agents and Moisturizers:

By the term "desquamating agent" is intended any compound capable of acting:

(a) either directly on desquamation by promoting exfoliation, such as β-hydroxy acids, in particular salicylic acid and derivatives thereof (including 5-n-octanoylsalicylic acid); α-hydroxy acids, such as glycolic acid, citric acid, lactic acid, tartaric acid, malic acid or mandelic acid; urea; gentisic acid; oligofucoses; cinnamic acid; extract of *Saphora japonica*; hydroxystilbenes including, in particular, resveratrol;

(b) or on the enzymes involved in the desquamation or degradation of corneodesmosomes, glycosidases, stratum corneum chymotryptic enzyme (SCCE), or even other proteases (trypsin, chymotrypsin-like). Exemplary agents for chelating mineral salts are EDTA; N-acyl-N,N',N'-ethylenediaminetriacetic acid; amino-sulfonic compounds and in particular (N-2-hydroxyethylpiperazine-N-2-ethane)sulfonic acid (HEPES); 2-oxothiazolidine-4-carboxylic acid (procysteine); .alpha.-amino acid derivatives of the type such as glycine (as described in EP-0,852,949); honey; sugar derivatives such as O-octanoyl-6-D-maltose and N-acetylglucosamine.

By the term "moisturizer" is intended:

(a) either a compound acting on the barrier function, in order to maintain the moisturization of the stratum corneum, or an occlusive compound. Exemplary are the ceramides, sphingoid-based compounds, lecithins, glycosphingolipids, phospholipids, cholesterol and derivatives thereof, phytosterols (stigmasterol, β-sitosterol or campesterol), essential fatty acids, 1,2-diacylglycerol, 4-chromanone, pentacyclic triterpenes, petroleum jelly and lanolin;

(b) or a compound that directly increases the water content of the stratum corneum, such as threalose and derivatives thereof, hyaluronic acid and derivatives thereof, glycerol, pentanediol, pidolates, amino acids (for examples serine, proline, glutamates, arginine), xylitol, urea, creatine, glucosamines, lactic acid, lactates, polyglyceryl acrylate, ectoin and derivatives thereof, chitosan, sugars, oligosaccharides and polysaccharides, cyclic carbonates, polyaspartate and derivates thereof, pyrrolidone-carboxylic acid and derivatives thereof, N-lauroyl-pyrrolidonecarboxylic acid, N-lauroyl-lysine and N-.alpha.-benzoyl-L-arginine;

(c) or a compound that activates the sebaceous glands, such as steroid derivatives (including DHEA) and vitamin D and derivatives thereof.

These compounds advantageously constitute from 0.001% to 30% and preferably from 0.01% to 20% of the total weight of the composition according to the invention.

The compositions according to the present invention comprising the desquamating agents and moisturizers indicated above are well suited for preventing or treating skin dryness and especially xerosis.

2. Depigmenting or Propigmenting Agents:

Exemplary depigmenting agents that may be formulated into the compositions according to the present invention comprise the following compounds: kojic acid; ellagic acid;

arbutin and derivatives thereof such as those described in EP-895,779 and EP-524,109; hydroquinone; aminophenol derivatives such as those described in WO-99/10318 and WO-99/32077, and in particular N-cholesteryloxycarbonyl-para-aminophenol and N-ethyloxycarbonyl-para-aminophenol; iminophenol derivatives, in particular those described in WO-99/22707; L-2-oxothiazolidine-4-carboxylic acid or procysteine, and also its salts and esters; ascorbic acid and derivatives thereof, especially ascorbyl glucoside; and plant extracts, in particular extracts of liquorice, of mulberry and of skullcap, this list not intended to be limiting.

Propigmenting agents that are exemplary include the extract of burnet (*Sanguisorba officinalis*) marketed by Maruzen, and extracts of chrysanthemum (*Chrysanthemum morifolium*).

The compositions according to the present invention comprising the depigmenting agents indicated above are well suited for preventing or treating hyperpigmentation, in particular pigmentary marks related to aging of the skin.

The compositions containing the propigmenting agents indicated above are well suited for treating baldness.

3. Anti-Glycation Agents:

By the term "anti-glycation agent" in intended a compound for preventing and/or reducing the glycation of skin proteins, in particular of dermal proteins such as collagen.

Exemplary anti-glycation agents are plant extracts of the Ericacea family, such as an extract of blueberry (*Vaccinium angustifolium*); ertothioneine and derivatives thereof; and hydroxystilbenes and derivatives thereof, such as resveratrol and 3,3',5,5'-tetrahydroxystilbene. These anti-glycation agents are described in FR-99/16166, FR-00/08158, FR-99/09267 and FR-99/16168, respectively. Resveratrol is particularly preferred for formulation into the compositions of the invention.

The compositions of the invention comprising an anti-glycation agent as defined above are well suited to prevent or treat the signs of aging of the skin, in particular to prevent or treat the loss of tonicity and/or elasticity of the skin.

4. NO-Synthase Inhibitors:

Exemplary NO-synthase inhibitors that are suitable for formulation into the compositions of the present invention especially comprise a plant extract of the species *Vitis vinifera* which is marketed by Euromed as Leucocyanidines de raisins extra, or by Indena under the trademark Leucoselect.®., or also by Hansen as Extrait de marc de raisin; a plant extract of the species *Olea europaea* which is preferably obtained from olive tree leaves and is marketed by Vinyals in the form of a dry extract, or by Biologia & Technologia under the trademark Eurol BT; and a plant extract of the species *Gingko biloba* which is preferably a dry aqueous extract of this plant marketed by Beaufour as *Gingko biloba* extrait standard.

The compositions according to the invention comprising an NO-synthase inhibitor as defined above are well suited to prevent or treat the signs of aging of the skin and/or sensitive skin.

5. 5α-reductase Inhibitors:

When the compositions according to the invention comprise a 5α-reductase inhibitor, such inhibitor is advantageously selected from among:

retinoids, and in particular retinol;

sulfur and sulfur derivatives;

zinc salts such as zinc lactate, gluconate, pidolate, carboxylate, salicylate and/or cysteate;

selenium chloride;

vitamin B6 or pyridoxine;

mixture of capryloyl glycine, sarcosine and extract of *Cinnamomum zeylanicum* marketed by Seppic under the trademark Sepicontrol A5.RTM.;

an extract of *Laminaria saccharina* marketed by SECMA under the trademark Phlorogine.RTM.;

an extract of *Spiraea ulmaria* marketed by Silab under the trademark Sebonormine™;

plant extracts from the species *Arnica montana, Cinchona succirubra, Eugenia caryophyllata, Humulus lupulus, Hypericum perforatum, Mentha piperita, Rosmarinus officinalis, Salvia oficinalis* and *Thymus vulgaris*, all marketed, for example, by Maruzen;

an extract of *Serenoa repens* marketed by Euromed;

plant extracts of the genus *Silybum*;

plant extracts containing sapogenins and in particular extracts of diosgenin-rich or hecogenin-rich *Dioscorea* plants; and extracts of *Eugenia caryophyllata* containing eugenol or eugenyl glucoside.

The 5α-reductase inhibitor advantageously constitutes, for example, from 0.001% to 10% and preferably from 0.01% to 5% of the total weight of the composition according to the invention. When this composition contains such a compound, it is particularly suitable for preventing or treating seborrhoea and/or hirsutism and/or androgen-dependent alopecia.

6. Lysyl and/or Prolyl Hydroxylase Inhibitors:

Preferred examples of lysyl and/or propyl hydroxylase inhibitors that may be formulated into the compositions according to the present invention are 2,4-diaminopyrimidine 3-oxide or 2,4-DPO described in WO-96/09048 and 2,4-diamino-6-piperidinopyrimidine 3-oxide or "Minoxidil" described in U.S. Pat. Nos. 4,139,619 and 4,596,812.

These compounds are advantageously present, for example, in the compositions of the invention in a proportion of from 0.001% to 5% by weight and preferably in a proportion of from 0.01% to 5% by weight relative to the total weight of the composition.

7. Agents for Stimulating the Synthesis of Dermal or Epidermal Macromolecules and/or for Preventing their Degradation:

Among the active agents for stimulating dermal macromolecules, exemplary are those that act:

(a) either on collagen synthesis, such as extracts of *Centella asiatica*; asiaticosides and derivatives thereof; ascorbic acid or vitamin C and derivatives thereof; synthetic peptides such as lamin, biopeptide CL or the palmitoyloligopeptide marketed by Sederma; peptides extracted from plants, such as the soybean hydrolysate marketed by Coletica under the trademark Phytokine.RTM.; plant hormones such as auxins and cinnamic acid and derivatives thereof, as described in the European patent application published under No. 0,925,779;

(b) or on elastin synthesis, such as the extract of *Saccharomyces cerivisiae* marketed by LSN under the trademark Cytovitin™.; and the extract of the alga *Macrocystis pyrifera* marketed by SECMA under the trademark Kelpadelie.RTM.;

(c) or on glycosaminoglycan synthesis, such as the product of fermentation of milk with *Lactobacillus vulgaris*, marketed by Brooks under the trademark Biomin yogourt®; the extract of the brown alga *Padina pavonica* marketed by Alban Muller under the trademark HSP®; and the extract of *Saccharomyces cerevisiae* available from Silab under the trademark Firmalift® or from LSN under the trademark Cytovitin®;

(d) or on fibronectin synthesis, such as the extract of the zooplankton Salina marketed by Seporga under the trademark GP4G®; the yeast extract available from Alban Muller under the trademark Drieline®; and the palmitoyl pentapeptide marketed by Sederma under the trademark Matrixil®;

(e) or on metalloprotease (MMP) inhibition, such as, more particularly, MMP 1, 2, 3 or 9: exemplary are the retinoids and derivatives, isoflavonoids, oligopeptides and lipopeptides, lipoamino acids, the malt extract marketed by Coletica under the trademark Collalift®; extracts of blueberry or of rosemary; carotenoids including, in particular, lycopene; isoflavones, their derivatives or plant extracts containing them, in particular extracts of soybean (marketed, for example, by Ichimaru Pharcos under the trademark Flavosterone SB®), of red clover, of flax, of kakkon, of sage or extracts of sage (as described in French patent application No. 00/10203);

(f) or on the inhibition of serine proteases such as leukocyte elastase or cathepsin G: exemplary are the peptide extract of Leguminosa seeds (*Pisum sativum*) marketed by LSN under the trademark Parelastyl®, and heparinoids and pseudodipeptides.

Among the active agents that stimulate epidermal macromolecules, such as fillagrin and keratins, especially representative are the extract of lupin marketed by Silab under the trademark Structurine®; the extract of beech *Fagus sylvatica* buds marketed by Gattefosse under the trademark Gatuline®, and the extract of the zooplankton Salina marketed by Seporga under the trademark GP4G®.

The compositions according to the invention containing one or more of the above compounds are particularly suitable for preventing or treating the signs of aging of the skin, in particular loss of firmness and/or elasticity of the skin.

8. Agents for Stimulating the Proliferation of Fibroblasts or Keratinocytes and/or Keratinocyte Differentiation:

Exemplary agents for stimulating the proliferation of fibroblasts that may be formulated into the compositions of the invention include plant proteins or polypeptides, extracts, especially of soybean (for example an extract of soybean marketed by LSN under the trademark Eleseryl SH-VEG8® or marketed by Silab under the trademark Raffermine®); and plant hormones such as giberrellins and cytokinins.

The agents for stimulating keratinocyte proliferation that may be formulated into the compositions according to the invention especially comprise retinoids such as retinol and its esters, including retinyl palmitate; retinoid acids and derivates thereof, extracts of nut cakes marketed by Gattefosse; and extracts of *Solanum tuberosum* marketed by Sederma.

The agents for stimulating keratinocyte differentiation comprise, for example, minerals such as calcium; the extract of lupin marketed by Silab under the trademark Photopreventine®; sodium beta-sitosteryl sulfate marketed by Seporga under the trademark Phytocohesine®; and the extract of corn marketed by Solabia under the trademark Phytovityl®.

The compositions according to the invention comprising these compounds are preferably used for preventing or treating the signs of aging of the skin.

9. Muscle Relaxants:

The muscle relaxants that may be included in the compositions according to the invention comprise calcium inhibitors such as alverine and its salts, chlorine-channel openers such as diazepam, and catecholamine and acetylcholine inhibitors, such as the hexapeptide argireline R marketed by Ilipotec.

The compositions of the invention comprising these compounds are used for preventing or treating the signs of aging of the skin and in particular wrinkles.

10. Antimicrobial Agents:

Exemplary antimicrobial agents that may be formulated into the compositions according to the invention include 2,4,4'-trichloro-2'-hydroxydiphenyl ether (or triclosan), 3,4,4'-trichloro-banilide, phenoxyethanol, phenoxypropanol, phenoxy-isopropanol, hexamidine isethionate, metronidazole and its salts, micronazole and its salts, itraconazole, terconazole, econazole, ketoconazole, saperconazole, fluconazole, clotrimazole, butoconazole, oxiconazole, sulphaconazole, sulconazole, terbinafine, ciclopirox, ciclopiroxolamine, undecylenic acid and its salts, benzoyl peroxide, 3-hydroxybenzoic acid, 4-hydroxy-benzoic acid, phytic acid, N-acetyl-L-cysteine acid, lipoic acid, azelaic acid and its salts, arachidonic acid, resorcinol, 2,4,4'-trichloro-2'-hydroxydiphenyl ether, 3,4,4'-trichlorocarbanalide, octopirox, octoxyglycerine, octanoylglycine, caprylyl glycol, 10-hydroxy-2-decanoic acid, dichlorophenylimidazole dioxolane and its derivatives described in WO-93/18743, farnesol and phytosphingosines, and mixtures thereof.

The preferred antimicrobial agents are triclosan, phenoxyethanol, octoxyglycerine, octanoyl-glycine, 10-hydroxy-2-decanoic acid, caprylyl glycol, farnesol and azelaic acid.

By way of example, the antimicrobial agents may be formulated into the compositions of the invention in amounts advantageously representing from 0.1% to 20% and preferably from 0.1% to 10% of the total weight of the composition.

11. Tensioning Agents:

By the term "tensioning agent" is intended a compound capable of exerting tension on the skin, the effect of which is to temporarily fade out irregularities on the skin's surface, such as wrinkles and fine lines.

Among the tensioning agents that may be formulated into the compositions of the present invention, especially representative are:

(1) polyurethane latices or acrylic-silicone latices, in particular those described in EP-1,038,519, such as a propylthio(polymethylacrylate), propylthio(polymethyl methacrylate) or propylthio(polymethacrylic acid) grafted polydimethyl-siloxane, or alternatively a propylthio(polyisobutyl methacrylate) and propylthio(polymethacrylic acid) grafted polydimethylsiloxane. Such grafted silicone polymers are marketed by 3M under the trademark VS 80, VS 70 or LO21.

(2) soybean or wheat plant proteins, and/or (3) sodium magnesium silicates (Laponites).

The compositions according to the invention comprising the above tensioning agents are well suited for treating the signs of aging of the skin, in particular wrinkles and fine lines.

12. Immunomodulatory Agents:

By the term "immunomodulatory agent" is intended any compound capable of either stimulate or suppress the immune response of the body, such as steroids, corticoids, azathioprine, mercaptopurines, methotrexate, mycophenolic acid and derivates thereof, leflunomide and derivates thereof, or cyclophosphamides.

13. Anti-Pollution Agents or Free-Radical Scavengers:

By the term "anti-pollution agent" is intended any compound capable of trapping ozone, monocyclic or polycyclic aromatic compounds such as benzopyrene and/or heavy metals such as cobalt, mercury, cadmium and/or nickel. By the term "free-radical scavenger" is intended any compound capable of trapping free radicals.

Exemplary ozone-trapping agents that may be formulated into the compositions according to the invention are, in particular, vitamin C and derivatives thereof, including ascorbyl glucoside; phenols and polyphenols, in particular tannins, ellagic acid and tannic acid; epigallocatechin and natural extracts containing same; extracts of olive tree leaf; extracts of tea, in particular of green tea; anthocyans; extracts of rosemary; phenol acids, in particular chlorogenic acid; stilbenes, in particular resveratrol; sulfur-containing amino acid derivatives, in particular S-carboxymethylcysteine; ergothioneine; N-acetylcysteine; chelating agents, for instance N,N'-bis(3,4,5-trimethoxybenzyl)ethylenediamine or one of its salts, metal complexes or esters; carotenoids such as crocetin; and various starting materials, for instance the mixture of arginine, histidine ribonucleate, mannitol, adenosine triphosphate, pyridoxine, phenyl-alanine, tyrosine and hydrolysed RNA, marketed by Laboratoires Serobiologiques under the trademark CPP LS 2633-12F®, the water-soluble fraction of corn marketed by Solabia under the trademark Phytovityl®, the mixture of extract of fumitory and of extract of lemon marketed under the trademark Unicotrozon C-49® by Induchem, and the mixture of extracts of ginseng, of apple, of peach, of wheat and of barley, marketed by Provital under the trademark Pronalen Bioprotect®.

Exemplary agents for trapping out monocyclic or polycyclic aromatic compounds according to the invention are, in particular, tannins such as ellagic acid; indole derivatives, in particular 3-indolecarbinol; extracts of tea, in particular of green tea, extracts of water hyacinth or *Eichhornia crassipes*; and the water-soluble fraction of corn marketed by Solabia under the trademark Phytovityl®.

Finally, exemplary heavy-metal-trapping agents that may be formulated into the compositions according to the invention include, in particular, chelating agents such as EDTA, the pentasodium salt of ethylenediamine tetramethylenephosphonic acid, and N,N'-bis(3,4,5-trimethoxybenzyl)ethylenediamine or one of the salts, metal complexes or esters thereof, phytic acid; chitosan derivatives; extracts of tea, in particular of green tea; tannins such as ellagic acid; sulfur-containing amino acids such as cysteine; extracts of water hyacinth (*Eichhornia crassipes*); and the water-soluble fraction of corn marketed by Solabia under the trademark Phytovityl®.

The free-radical scavengers that may be included in the compositions according to the invention comprise, other than certain anti-pollution agents indicated above, vitamin E and derivatives thereof such as tocopheryl acetate; bioflavonoids; coenzyme Q10 or ubiquinone; certain enzymes, for example, catalase, superoxide dismutase, lactoperoxidase, glutathione peroxidase and quinone reductases; glutathione; benzylidenecamphor; benzylcyclanones; substituted napthalenones; pidolates; phytanetriol; gamma-oryzanol; lignans; and melatonin.

The compositions of the invention comprising the anti-pollution agents and/or free-radical scavengers indicated above are well suited for preventing or treating the signs of aging of the skin, in particular wrinkles, and loss of firmness and elasticity of the skin and dehydration. As a variant, same are useful for preventing or treating a dull complexion.

14. UVA and/or UVB Screening Agents and Optionally Coated Inorganic Pigments:

The compositions according to the invention may contain one or more UV-screening agents capable of screening out UVA and/or UVB radiation.

Exemplary compounds for screening out UVA radiation include, especially:

(a) benzophenone derivatives, for example:

2,4-dihydroxybenzophenone(benzophenone-1);

2,2',4,4'-tetrahydroxybenzophenone(benzo-phenone-2);

2-hydroxy-4-methoxybenzophenone(benzo-phenone-3), available from BASF under the trademark Uvinul M40;

2-hydroxy-4-methoxybenzophenone-5-sulfonic acid (benzophenone-4) and also its sulfonate form (benzophenone-5), available from BASF under the trademark Uvinul MS40;

2,2'-dihydroxy-4,4'-dimethoxybenzophenone(benzophenone-6);

5-chloro-2-hydroxybenzophenone(benzophenone-7);

2,2'-dihydroxy-4-methoxybenzophenone(benzo-phenone-8);

the disodium salt of 2,2'-dihydroxy-4,4'-dimethoxybenzophenone-5,5'-disulfonic acid (benzophenone-9);

2-hydroxy-4-methoxy-4'-methylbenzophenone(benzophenone-10);

benzophenone-11;

2-hydroxy-4-(octyloxy)benzophenone(benzo-phenone-12);

benzophenones 3 and 5 being preferred;

(b) triazine derivatives, and in particular 2,4-bis {[4-(2-ethylhexyloxy)-2-hydroxy]phenyl}-6-(4-methoxy-phenyl)-1,3,5-triazine available from Ciba Geigy under the trademark Tinosorb S and 2,2'-methylenebis[6-(2H-benzotriazol-2-yl)-4-(1,1,3,3-tetramethylbutyl)phenol] available from Ciba Geigy under the trademark Tinosorb M;

(c) benzene-1,4-bis(3-methylidene-10-camphorsulfonic acid), optionally in partially or totally neutralized form, and (d) mixtures thereof.

Exemplary compounds for screening out UVB radiation include:

(a) salicylic acid derivatives, in particular homomenthyl salicylate and octyl salicylate;

(b) cinnamic acid derivatives, in particular 2-ethylhexyl p-methoxycinnamate, available from Givaudan under the trademark Parsol MCX;

(c) liquid .beta.,.beta.'-diphenylacrylate derivatives, in particular 2-ethylhexyl .alpha.-cyano-.alpha.,.beta.'-diphenylacrylate, or octocrylene, available from BASF under the trademark Uvinul N539;

(d) p-aminobenzoic acid derivatives;

(e) 4-methylbenzylidenecamphor available from Merck under the trademark Eusolex 6300;

(f) 2-phenylbenzimidazole-5-sulfonic acid marketed under the trademark "Eusolex 232" by Merck;

(g) 1,3,5-triazine derivatives, in particular: and 2,4,6-tris[p-(2'-ethylhexyl-1'-oxycarbonyl)anilino]-1,3,5-triazine, available from BASF under the trademark Uvinul T150.

Exemplary compounds for screening out UVA and UVB radiation are, in particular:

plant extracts, in particular of rosemary (rosmarinic acid) and of the genus *Leontopodium*, in particular a plant species *Leontopodium alpinum* or *Leontopodium stracheyi*; and benzotriazole silicone, described in FR-A-2,642,968.

Exemplary optionally coated inorganic pigments include nanopigments of titanium dioxide, of iron oxide, of zinc oxide, of zirconium oxide or of cerium oxide optionally coated with alumina and/or with aluminum stearate.

15. Compounds of Neurogenic Origin for Reducing Irritation:

Exemplary compounds of neurogenic origin for reducing irritation include:

(a) substance P antagonists and in particular those described in EP-0,680,749, extracts of at least one non-photosynthetic filamentous bacterium, particularly strains of *Vitreoscilla filiformis* described in EP-0,761,204, the spring waters described in EP-0,764,440, extracts of at least one plant of the Rosacea family, particularly of the species *Rosa gallica* described in the European patent application published under No. 0,906,752 and the alkaline earth metals described in the European patent applications published under Nos. 0,737,471 and 0,770,302;

(b) CGRP antagonists, in particular those described in EP-0,765,668 and especially Iridacea extracts, particularly of the species *Iris pallida;*

(c) NO-synthase inhibitors;

(d) bradykinin antagonists and in particular those described in the European patent application published under No. 0,909,556;

(e) cytokine antagonists;

(f) histamine antagonists;

(g) antagonists of interleukin 1 and/or of tumor necrosis factor of α type (TNFα) and in particular those described in the European patent applications published under Nos. 0,892,642 and 0,764,444, particularly peptide Modulene, the tripeptide Lysine-Proline-Valine (KPV) and an extract of at least one plant from the Labiae family, particularly of the species *Rosmarinus officinalis;*

(h) sodium-channel blockers preferably selected from among: Amiloride, Quinidine, Quinidine sulfate, Apamine, Cyproheptadine, Loperamide and N-acetylprocainamide (i) potassium-channel openers, especially Minoxidil and derivatives thereof.

The composition should also comprise a vehicle to enable the active ingredient to be conveyed to the skin in an appropriate dilution. The composition may be in a form of liquid, suspension, emulsion, lotion or cream.

The selection of a vehicle for the active ingredient(s) in compositions of the invention presents a wide range of possibilities depending on the required product from of the composition. Suitable vehicles can be classified as described hereinafter.

It should be explained that vehicles are substances which can act as diluents, dispersants, or solvents for the active ingredients and which therefore ensure that they can be applied to and distributed evenly over the skin at an appropriate concentration; the vehicle is preferably one which can aid penetration of the active ingredient into the skin, thus ensuring that the effectiveness of the active ingredient is prolonged because of improved properties. Compositions according to this invention can include water is a vehicle, and/or at least one cosmetically acceptable vehicle other than water.

Vehicles other than water that can be used in compositions according to the invention can include solids or liquids such as emollients, propellants, solvents, humectants, thickeners and powders. Examples of each of these types of vehicles, which can be used singly or as mixtures of one or more carriers, are as follows:

Emollients, such as stearyl alcohol, glyceryl monoricinoleate, glyceryl monostearate, propane-1,2-diol, butane-1,3-diol, mink oil, cetyl alcohol, isopropyl isostearate, stearic acid, isobutyl palmitate, isocetyl stearate, oleyl alcohol, isopropyl laurate, hexyl laurate, decyl oleate, octadecan-2-ol, isocetyl alcohol, cetyl palmitate, dimethylpolysiloxane, di-n-butyl sebacate, isopropyl myristate, isopropyl palmitate, isopropyl stearate, butyl stearate, polyethylene glycol, triethylene glycol, lanolin, castor oil, acetylated lanolin alcohols, petroleum, mineral oil, butyl myristate, isostearic acid, palmitic acid, isopropyl linoleate, lauryl lactate, myristyl lactate, decyl oleate, myristyl, myristate;

Propellants, such as trichlorofluoromethane, dichlorodifluoromethane, dichlorotetrafluorethane, monochlorodigluoromethane, trichlorotrifluorethane, propane, butane, isobutane, dimethyl ether, carbon dioxide, nitrous oxide;

Solvents, such as ethyl alcohol, methylene chloride, isopropanol, castor oil, ethylene glycol monoethyl ether, diethylene glycol monobutyl ether, diethylene glycol monoethyl ether, dimethyl sulphoxide, tetrahydrofuran;

Humectants, such as glycerin, sorbitol, sodium 2-pyrrolidone-5-carboxylate, soluble collagen, dibutyl phthalate, gelatin; and Powders, such as chalk, talc, fullers, earth, kaolin, starch, gums, colloidal silicon dioxide, sodium polyacrylate, tetra alkyl and/or trialkyl aryl ammonium smectites, chemically modified magnesium aluminium silicate, organically modified montmorillonite clay, hydrated aluminium silicate, fumed silica, carboxyvinyl polymer, sodium carboxymethyl cellulose, ethylene glycol monostearate.

The amount of vehicle in the composition, including water if present, should preferably be sufficient to carry at least a portion of the active ingredient to the skin in an amount which is sufficient effectively to provide skin benefit. The amount of the vehicle can comprise the major portion of the composition, particularly where little or no other ingredients are present in the composition.

The composition will accordingly comprise from 15 to 99.989% and preferably from 50 to 99.5% by weight of the vehicle or vehicles.

The composition according the invention can contain ingredients other than those already mentioned, depending on the form of the intended product. It is, for example, possible to include antiseptics, preservatives, antioxidants, emulsifiers, colouring agents and detergents, some of which are described in detail above.

The composition according to the invention can also be employed as a vehicle for a wide variety of cosmetically or pharmaceutically active ingredients, particularly ingredients which have some beneficial effect when applied to the skin.

The composition thus provides a means whereby such active ingredients can be diluted, dispersed, conveyed to and distributed on the skin surface at an appropriate concentration.

The invention also provides a kit for skin care or treatment, comprising: a vessel containing the inventive composition, optionally further comprising instruction of how to use the inventive composition.

The inventive composition may also be embedded in a mask for the face or the body. The mask may comprise a backing sheet containing the inventive composition serving to exert a specific action on the skin. The backing sheet may be in a dry or web state, preferably stretchable at least in the wet state, in order to enable the mask to be adapted to fit the shape of the face or of the portion of the body to be treated. The backing sheet may be made of paper, fabric, cloth, or a polymeric material.

The invention also provides a process for the preparation of a cosmetic composition for topical application to skin which comprises mixing an active ingredient, as herein defined, with a suitable vehicle to provide a concentration of from 0.001% to 0.5%.

The compositions of the invention can be formulated as liquids, for example as a lotion or milk for use in conjunction with an applicator such as a roll-ball applicator, or a spray device such as an aerosol can containing propellant, or a container fitted with a pump to dispense the liquid product. Alternatively, the compositions of the invention can be solid or semi-solid, for example sticks, creams or gels, for use in conjunction with a suitable applicator or simply a tube, bottle or lidded jar, or as a liquid-impregnated fabric, such as a tissue wipe.

Preferably the composition is an aqueous emulsion and this can be a water-in-oil emulsion, or an oil-in-water emulsion. A particularly important composition or the invention is an aqueous fat emulsion in which the aqueous phase of the emulsion acts as a carrier.

Pharmaceutical compositions for topical application are particularly important, for skin condition is dependent on the presence of essential fatty acids, Such a composition can be liquid or plastic: liquid compositions include oils comprising the inventive composition with or without additional carrier oil; lotions, such as a solution in a physiologically acceptable solvent of an ester of the invention in free or derivative form, for instance an aqueous solution or an aqueous emulsion of the ester; and creams and ointments, such as a plastic dispersion of the ester in free or derivative form in a suitable carrier, for instance an ointment base. Such compositions are useful in the prevention and cure of skin damage caused by contact with detergents, and in treating environmental trauma due to weathering, sunburn, burns of other types and in reducing bacterial activity on the skin.

The invention accordingly also provides a closed container containing a cosmetic composition as herein defined.

Compositions of the invention are intended especially for topical application to human skin, in particular when the skin surface has become excessively dry, fissured, eroded or otherwise damaged.

The invention accordingly also includes a process of topical administration of the composition of the invention to human subjects suffering from or liable to suffer from excessively dry, fissured, eroded or otherwise damaged skin and other skin disorders. The dosage rate will depend on the condition to be treated as well as the route of administration. Local skin symptoms may require one or more applications of the composition.

The invention also provides for the use of an active ingredient, as herein defined, in the topical treatment of skin disorders.

The effectiveness of the inventive compositions on the promotion or restoration of the skin barrier function may be evaluated by using experimental animal models or tested on human subjects.

The model experimental animals usable in the present invention are those commonly used as experimental animals for various tests other than humans. Any animal may be used so long as in line with the object of the present invention, but usually rats, guinea pigs, rabbits, etc. are used.

The animals may be subjected to means for reducing the skin barrier function. The means may be any method capable of reducing the skin barrier function efficiently. The format of the means does not matter. To cause this reduction, it is convenient to remove the corneal layer of the epidermis by tape stripping or remove the corneal layer by treatment with a surfactant (for example, sodium dodecyl sulfate (SDS)) or an organic solvent such as acetone. As the timing of treatment, in the case of rats, e.g., after about 12 hours from the end of the application of the stress is preferable in ensuring a sufficient state of stress to the experimental animals.

The degree of recovery of the skin barrier function at the location of reduction of the skin barrier due to the above is detected over time or after a predetermined time interval. The location where the reduction is caused may be any location of the experimental animals so long as it enables detection of the degree of recovery of the skin barrier function, but usually it is preferable to select the auricle, that is, the projecting outer portion of the ear.

The method of detection may be to measure the transepidermal water loss or the transdermal insensible perspiration (TEWL)—generally considered an indicator of the skin barrier function, but it might be possible to use other factors capable of serving as indicators as well. The TEWL may be measured by a commercially available equipment itself in common use. As typical equipment, an Evaporimeter, a Tewameter, Micromoisture measurer, etc. may be mentioned.

For example, the effects of the inventive compositions on the promotion or restoration of skin barrier function can be tested on human subjects using an instrument for transepidermal water loss measurement, e.g., Tewameter TM-210 (Courage+Khazaka electronic, Cologne, Germany). For example, human subjects are allowed to rest and relaxed for 15-30 before the measurements started in an air-conditioned room, under constant temperature (21 degree celcius) and humidity 30-50%, with the skin at the measuring site left uncovered. The instrument is allowed to warm-up for 15 minutes after being turned on. The calibration is checked and the baseline value is set to zero once for all subsequent measurements. The measuring probe is placed perpendicular to the skin in a horizontal plane until stabilization of values is reached, about 60 seconds after the placement of the probe. Continuous holding by hand or any heat transfer to the probe is avoided. The contact pressure of the probe onto the skin is kept low and constant.

To test the effects of the inventive compositions on skin barrier function, experimental animals or human volunteers can be used. For example, on a human volunteer volunteer, several sites on the volar forearm are identified. The composition to be tested and placebo are applied randomly on those sites. At the determined time-points (varied according to the environment and subject conditions) the measurements of transepidermal water loss are taken. The data are tabulated and analyzed statistically.

Optionally, the effects of the inventive compositions on the promotion or restoration of skin barrier function can be tested on human subjects using an instrument for skin surface hydration measurement, e.g., Corneometer CM825 (Courage+Khazaka electronic, Cologne, Germany). For example, human subjects are allowed to rest and relaxed for 15-30 before the measurements started in an air-conditioned room, under constant temperature (21 degree celcius) and humidity 30-50%, with the skin at the measuring site left uncovered. The instrument is allowed to warm-up for 5 minutes after being turned on. The probe is wiped clean with a tissue paper soaked in 70% ethanol and zeroed against a dry clean surface (table or bench top) to establish the integrity of the instrument (reading should be less than 5). To obtain the reading 3 measurements are made within a skin skite and subsequently averaged. The probe is held by the handle only, gently placed perpendicular to the surface of the skin and depressed until the outer chamber of the probe comes in contact with the skin. The same pressure is exerted for all measurements, avoiding excess pressure. The instrument gives a beep sound when the measurement is complete.

Before each subsequent measurement, the surface of the probe is wiped by the tissue paper soaked in 70% ethanol and the probe is re-zeroed against a dry surface. For example, on each volunteer, several sites on the volar forearm are identified. The formulation to be tested and placebo are applied randomly on those sites. At the determined time-points (varied according to the environment and subject conditions) the measurements of skin surface hydration are taken. The data are tabulated and analyzed statistically.

This present invention also provides a method for treating undesirable or pathological skin conditions of a mammal. The method comprises: topically applying to the skin of the mammal a composition comprising about 0.01-8% w/w divalent calcium ions and/or divalent magnesium ions based on the total weight of the composition in a physiologically acceptable medium for such period of time as required to elicit the desired cosmetic/therapeutic response. Examples of the undesirable skin condition include, but are not limited to, adverse signs of aging of the skin, a dull complexion, skin or hair pigmentation disorders, skin dryness, hyperseborrhoea, hyperseborrhoea-related imperfections, sensitive skin, dandruff, natural hair loss, and baldness. Examples of pathological skin condition include, but are not limited to, the dermatologic diseases linked to a keratinization disorder (differentiation-proliferation), inflammation and/or immunoallergy, such as acne vulgaris, blackheads or polymorphes, acne seniles, sunlight and medicinal or professional acne, rosacea, extensive and/or severe forms of psoriasis, and other keratinization disorders such as ichtyosis and ichtyosis-like states, Darier illness, palmoplantary keratodermies, leucoplasies and leucoplasie-like states, lichen plan, all benign or malignant dermatologic proliferations, extensive or severe, rheumatoid psoriases, pruritus; erythmas, atopic dermatitis, contact dermatitis, contact eczema, lichen planus, prurigo, urticaria, pruriginous toxidermia, and hyperkeratosis.

Each citation indicated above, whether of the open literature, patent, patent application, or otherwise, is hereby expressly incorporated by reference.

In order to further illustrate the present invention and the advantages thereof, the following specific examples are given, it being understood that same are intended only as illustrative and in nowise limitative.

In said examples to follow, all parts and percentages are given by weight.

EXAMPLES

Example 1

Toner Solution

This example describes an embodiment of the compositions according to the invention, which is an aqueous solution and may be used as skin toner. The ingredients of the solution are listed as follows.

| | |
|---|---|
| Sodium chloride | 2.13% |
| Potassium chloride | 0.48% |
| Potassium bromide | 0.54% |
| Magnesium chloride | 2.02% |
| Calcium chloride | 2.06% |
| Glycerin | 1.02% |
| Water | 91.54% |
| Preservatives | 0.21% |

This solution contains combination of calcium ions with other salts in a composition to restore homeostatis of major ionic components in skin. The ratio of the monovalent ions: potassium and sodium from NaCl, KCl, KBr are balanced with divalent ions from $MgCl_2$ and $CaCl_2$. The mixture was prepared with attention not to cause "salting-out" phenomenon, in which less water-soluble salts were forced to crystalize after the addition of more water-soluble ones. The glycerin was used to maintain the viscosity of the solution.

Briefly, the solution in this example was prepared according to the following procedure. Sodium chloride, potassium chloride and potassium bromide were dissolved thoroughly into purified water by stirring. Thereafter, magnesium chloride and calcium chloride were added in a consecutive order while stirring until each one was totally dissolved. Glycerin and the preservative were then added. Before filling, the solution was passed through a 0.2-μm filter to rid of undissolved particles or other impurities.

Example 2

Skin Care Cream

This example describes an embodiment of the compositions according to the invention, which is a water-oil emulsion and may be used as skin care cream. The ingredients of the emulsion (designated as Cream Formulation I) are listed as follows.

| | |
|---|---|
| Pentaerythrityl tetracaprylate/tetracaprate | 5.2% |
| Emulsifying Wax | 3.9% |
| Behentrimonium methosulfate (and) cetearyl alcohol | 3.15% |
| Mineral Oil | 0.88% |
| Soybean Oil | 1.06% |
| Lanolin alcohol | 0.51% |
| Water | 81.72% |
| Calcium chloride | 0.22% |
| Glycerin | 1.9% |
| Wheat ammo acids | 0.53% |
| Preservatives | 0.93% |
| Fragrance | q.s. |

In a variant of this embodiment, a water-oil emulsion was prepared with ingredients listed above except that the concentration of calcium chloride is reduced, and other divalent cations such as magnesium, as well as monovalent cations such as sodium and potassium, were added. The ingredients of this emulsion (designated as Cream Formulation II) are listed as follows.

| | |
|---|---|
| Pentaerythrityl tetracaprylate/tetracaprate | 5.2% |
| Emulsifying Wax | 5.89% |
| Behentrimonium methosulfate (and) cetearyl alcohol | 3.15% |
| Mineral Oil | 0.88% |
| Soybean Oil | 1.06% |
| Lanolin alcohol | 0.51% |

-continued

| | |
|---|---|
| Water | 79.58% |
| Calcium chloride | 0.104% |
| Magnesium chloride | 0.102% |
| Sodium chloride | 0.108% |
| Potassium chloride | 0.027% |
| Potassium bromide | 0.029% |
| Glycerin | 1.9% |
| Wheat amino acid | 0.53% |
| Preservatives | 0.93% |
| Fragrance | q.s. |

According to this embodiment of the invention, the water-oil emulsion provides calcium ions (which are optionally balanced with other divalent cations such as magnesium, as well as monovalent cations such as sodium and potassium), natural amino acids and essential skin lipid components. It is believed that by combining calcium ions with natural amino acids and/or essential skin lipid components, unwanted or adverse effects triggered by exogeneous calcium may be avoided. This is because applying calcium alone to the skin may force the skin to use low quality substitutes from the skin for building the skin barrier, especially when the skin is already damaged or in a pathological condition. Thus, the cream can supplement the skin with necessary "building blocks" for construction and restoration of the skin barrier.

In the cream, lanolin alcohol contains cholesterol, and the soybean oil provides fatty acids and short chain lipids essential to the skin. Wheat amino acids supply the materials necessary for naturally moisturizing the skin. The mixture of calcium chloride in glycerin-water is preferably added slowly to the lipid mixture at the designated temperature to avoid sudden precipitation of low molecular weight lipids by forming complex with calcium ions. The surfactants used have certain delivery capability to deliver the essential components to the target site in the skin.

Briefly, the cream in this example was prepared according to the following procedure. Pentaerythrityl tetracaprylate/tetracaprate, emulsifying wax, behentrimonium methosulfate and cetearyl alcohol, mineral oil, soybean oil and lanolin alcohol were added to a manufacturing vessel, and the vessel was stirred and heated to 75° C. Calcium chloride was dissolved into water and glycerin was then added. The aqueous solution was heated to 75° C. and added into the manufacturing vessel with quick stirring, resulting in a mono-phase emulsion. The vessel was cooled down to 40° C. When the desired temperature was reached, wheat amino acids, preservatives and fragrance was added and mixed thoroughly in the vessel.

Example 3

Skin Care Gel

This example describes an embodiment of the compositions according to the invention, which is a silicone-based gel and may be used as skin care gel. The ingredients of the gel are listed as follows.

| | |
|---|---|
| Cyclopentasiloxane (and) dimethicone crosspolymer (and) cyclohexasiloxane | 70.44% |
| Cyclomethicone | 19.52% |
| Propylene glycol | 3.64% |

-continued

| | |
|---|---|
| Soluble collagen | 0.49% |
| Hydrolized silk protein | 0.72% |
| Tocopheryl acetate | 0.45% |
| Glycerin | 2.98% |
| Marine collagen amino acids | 0.53% |
| Calcium chloride | 0.21% |
| Preservatives | 1.02% |

This formulation combines calcium ions with amino acids for enhancing collagen production and anti-aging properties. It is believed that adding exogenous calcium alone may not be sufficient for promoting collagen production in skin. The soluble collagen in the gel is intended to give direct supply of such an essential skin component whereas the collagen amino acids supply the building blocks for synthesis of collagen and elastin. In this formulation it is preferred that no water was added, although moderate amount of water should not be harmful.

Briefly, the gel in this example was prepared according to the following procedure. The mixture of cyclopentasiloxane, dimethicone crosspolymer, cyclohexasiloxane (e.g., Silicone Elastomer Blend) was added to cyclomethicone and stirred in a manufacturing vessel. Propylene glycol, soluble collagen, hydrolized silk protein, tocopheryl acetate, glycerin, marine collagen amino acids, calcium chloride and preservatives were mixed in separate vessel, and then added into the manufacturing vessel with continuous moderate stirring. Care was taken with stirring to avoid too much aeration.

Example 4

Skin Cleansing Lotion

This example describes an embodiment of the compositions according to the invention, which may be used as skin cleanser. The ingredients of the skin cleansing lotion are listed as follows.

| | |
|---|---|
| Water | 69.95% |
| Decyl Oleate | 2.28% |
| Sodium Lauryl Sulfate | 4.96% |
| Stearic Acid | 3.18% |
| Lauramide DEA | 1.25% |
| Glyceryl Stearate S.E. | 2.47% |
| Cetyl Alcohol | 1.98% |
| Propylene glycol | 2.37% |
| Triethanolamine | 0.24% |
| Phospholipids | 0.82% |
| 1,3-Butylene glycol | 0.69% |
| Cholesterol | 0.36% |
| Tocopheryl Acetate | 0.21% |
| Thiamine Mononitrate | 0.09% |
| Niacin | 0.11% |
| Calcium D-Panthothenate | 0.12% |
| Pyridoxine | 0.04% |
| Ascorbic Acid | 0.12% |
| Retinyl Palmitate | 0.05% |
| Cholecalciferol | 0.06% |
| Phytonadione | 0.09% |
| Polysorbate-80 | 8.11% |
| Diazolidinyl Urea | 0.29% |
| Methyl paraben | 0.11% |
| Propyl paraben | 0.05% |

The inventors believe that the use of skin cleansers with excessive solubilization strength can extract out water-soluble components out of the skin, including ions of calcium, magnesium, sodium, potassium, and many others. To prevent such extraction of the vital minerals, the inventive cleanser is provided, which, when applied to the skin and washed off, leaves a thin fatty layer on the surface of the skin after cleansing. Such a layer is formed by incorporating fatty film forming ingredients in the cleanser such as Decyl Oleate, Lauramide DEA, and Glyceryl Stearate S.E.

Example 5

In Vitro Study to Assess Change of Calcium Ion Distribution in Epidermis

This example describes an in vitro study undertaken to assess the change of the calcium ion distribution in epidermis before and after the application of the toner formulation described in Example 1 and Cream Formulation II in Example 2.

1) Materials and Methods

Standards: Calcium chloride in 20% (w/v) gelatin dissolved in hot, distilled water with 5% glycerin. Standards were quench frozen (in Freon) at approximately −190° C. and cryosectioned (at −20° C.) to a thickness of 12-16 µm, then they were freeze-dried Samples: Fresh human abdominal skin membrane was obtained from surgery. After removal of fat, the skin membrane was washed using 10% aqueous sodium lauryl sulfate solution for 3 hours at 25° C. to deprive the minerals. After dried in the air, the skin was cut into several pieces. Some pieces were left untreated. The epidermal surface of the remaining pieces was treated for 30 minutes with the subsequent application of the toner formulation described in Example 1 and Cream Formulation II in Example 2. Then, the surface was dried with tissue paper to remove excessive materials. All samples (treated and untreated) were quench frozen (in Freon) at approximately −190° C. and cryosectioned (at −20° C.) to a thickness of 15-20 µm, then they were freeze-dried.

Analysis: Analysis was performed using Proton Induced X-Ray Emission (PIXE) Method. Samples were mounted between two supporting foils. Proton of 2.5 MeV from an electrostatic accelerator (Pelletron 3UDH) were collimated and focused by quadrupole magnets to form a rectangular beam spot at the sample of 5-10×100 µm$^2$. The proton current density was 1.2 pA/µm$^2$. The total charge accumulated in each analysis was 0.1 µC and the X-rays were detected in a Kevex Si(Li) detector (80 mm$^2$, internally collimated to 60 mm$^2$, FWHM=160 eV at 5.9 keV).

2) Results

Figure 1:
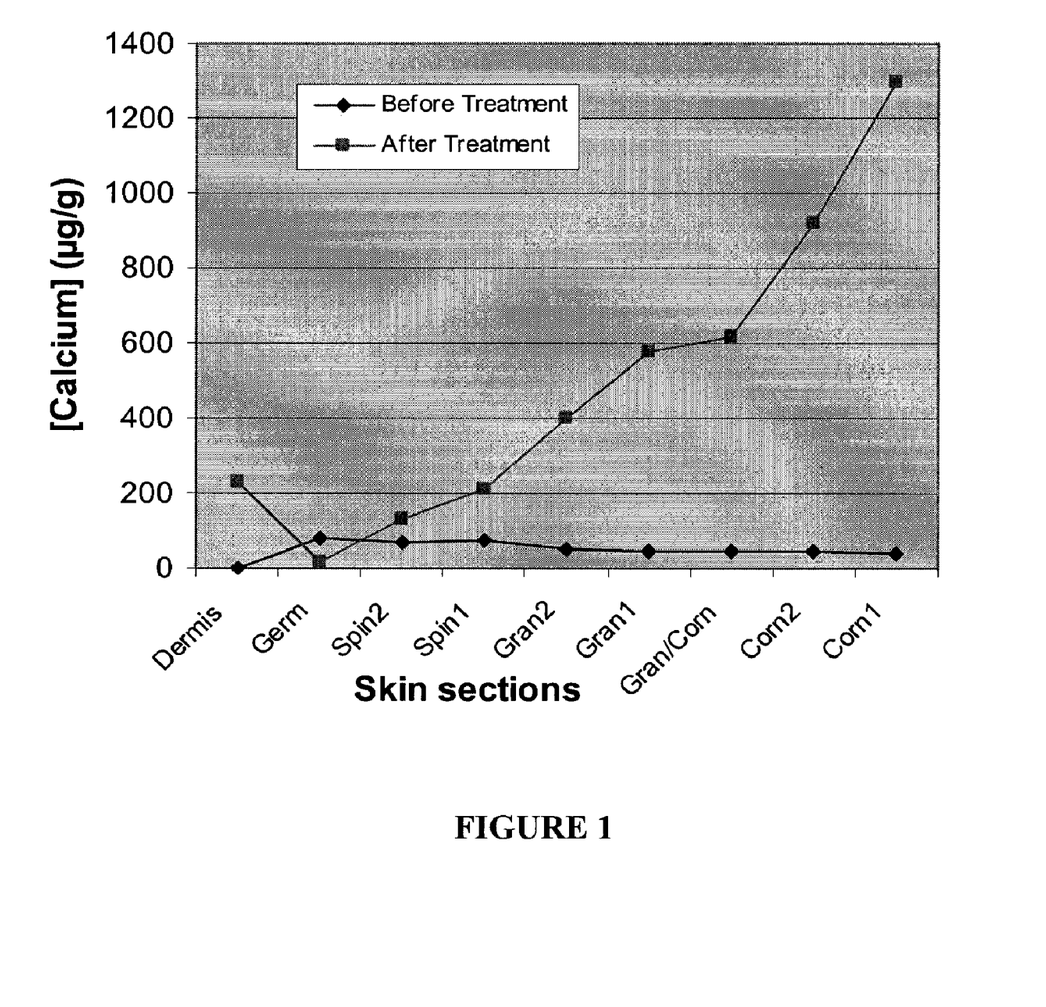
FIG. 1 is a plot showing calcium concentration in skin sections from the upper layer (Corn1) to the deeper epidermis (Germ) and dermis, before and after treatment with an embodiment of the toner and cream according to the present invention. (Corn: stratum corneum; Gran: stratum granulosum; Spin: stratum spinosum; Germ: stratum germinativum/basale)

The calcium concentration in each skin sections was assessed. As shown in FIG. 1, the untreated skin sections ("Before treatment") showed low calcium concentration. The treated sections ("After treatment") showed a concentration gradient of calcium ions which was higher at the upper layers (close to the skin surface) and lower in the deeper epidermis. This pattern of calcium concentration gradient is very similar to the pattern reported in the literature for normal skin. See Malmqvist et al. (1987) "The use of PIXE in experimental studies of the physiology of human skin epidermis", Biol. Trace Elem. Res. 12:297-308; and Pallon et al. (1996) "Pixe analysis of pathological skin with special reference to psoriasis and atopic dry skin," Cell Mol Biol (Noisy-le-grand) 42 (1):111-8.

3) Conclusion

This in vitro study showed that the inventive toner and cream can deliver calcium ions into skin and achieve the restoration the calcium concentration gradient of mineral deprived skin membranes to the pattern found in normal skin.

Example 6

In Vivo Study to Assess Effects of Inventive Toner and Cream on Restoration of Skin Barrier Function This example describes an in vitro study undertaken to assess the effects of the toner formulation described in Example 1 and Cream Formulation II in Example 2 on the restoration of skin barrier function by using Transepidermal Water Loss (TEWL) measurements.

1) Materials and Methods

Five human subjects with normal skin, with age ranging from 25 to 45, participated in the study. The TEWL measurements were performed using Tewameter TM-210 (Courage+Khazaka, Germany) on two volar forearm sites of the same arm each subject. After a period of acclimatization, TEWL measurements were taken to assess the baseline values. The sites were intentionally damaged by stripping 15 times using Scotch Tape, but not fully removing the epidermis. One site was left untreated but covered with gauze. The other site was treated with the subsequent application of the skin toner described in Example 1 and Cream Formulation II in Example 2 twice a day with 8 hour interval. Once a day prior to the treatment, the TEWL on the sites were measured. This was repeated up to 5 days after the tape stripping.

Figure 2:
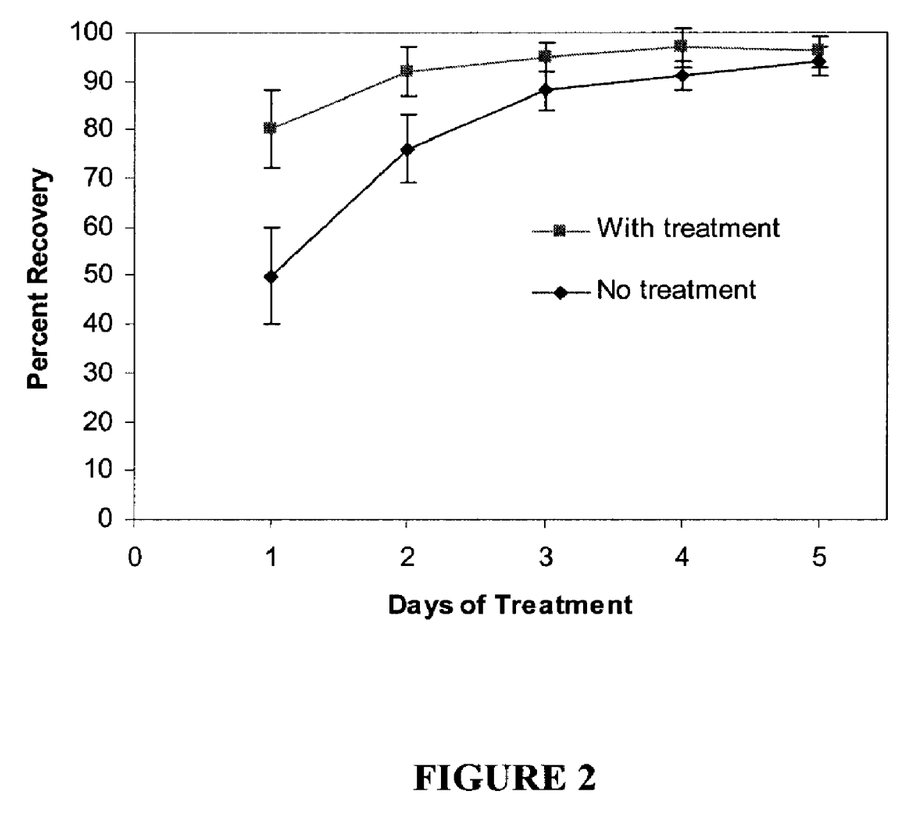
FIG. 2 is a plot showing recovery progress of skin damaged by tape-stripping with or without treatment using an embodiment of the toner and cream according to the present invention. Percent recovery is calculated based on TEWL (transepidermal water loss) baseline values/TEWL each day prior to the treatment.

2) Results:

FIG. 2 showed the progress of skin barrier restoration, calculated as the TEWL baseline values/TEWL after the stripping and treatments. Without treatments, living human skin showed capacity to recover. The treatment of the inventive toner and cream accelerated the recovery process in the first 3 days after the skin damage by stripping.

3) Conclusion

Application of the inventive toner and cream can accelerate barrier restoration compared to the site without application.

Example 7

In Vivo Study to Assess Effects of Inventive Toner and Cream on Human Subjects with Known Condition of Dry Skin This example describes an in vivo study undertaken to assess the effect of the toner formulation described in Example 1 and Cream Formulation II in Example 2 on subjects with known condition of dry skin.

1) Materials and Methods

A total of 30 subjects, male and female aged 17 to 60 years, with minimal to mild dry skin symptoms in low leg area, participated in the study. Each subject was given a set of toner formulation described in Example 1 and Cream Formulation II in Example 2 to be applied to the symptomatic area twice daily for two weeks. The daily self-evaluation was documented on the score of scaling and/or erythema on the Clinical Research Form (CRF). On week 2 the CRF was collected from the subjects for data analysis.

Safety evaluation: Safety was assessed from vital signs, signs and symptoms of applied skin, and reported adverse experiences.

Efficacy evaluation: To determine the efficacy, the time to reach no clinical sign of scaling was used as parameter.

Figure 3:
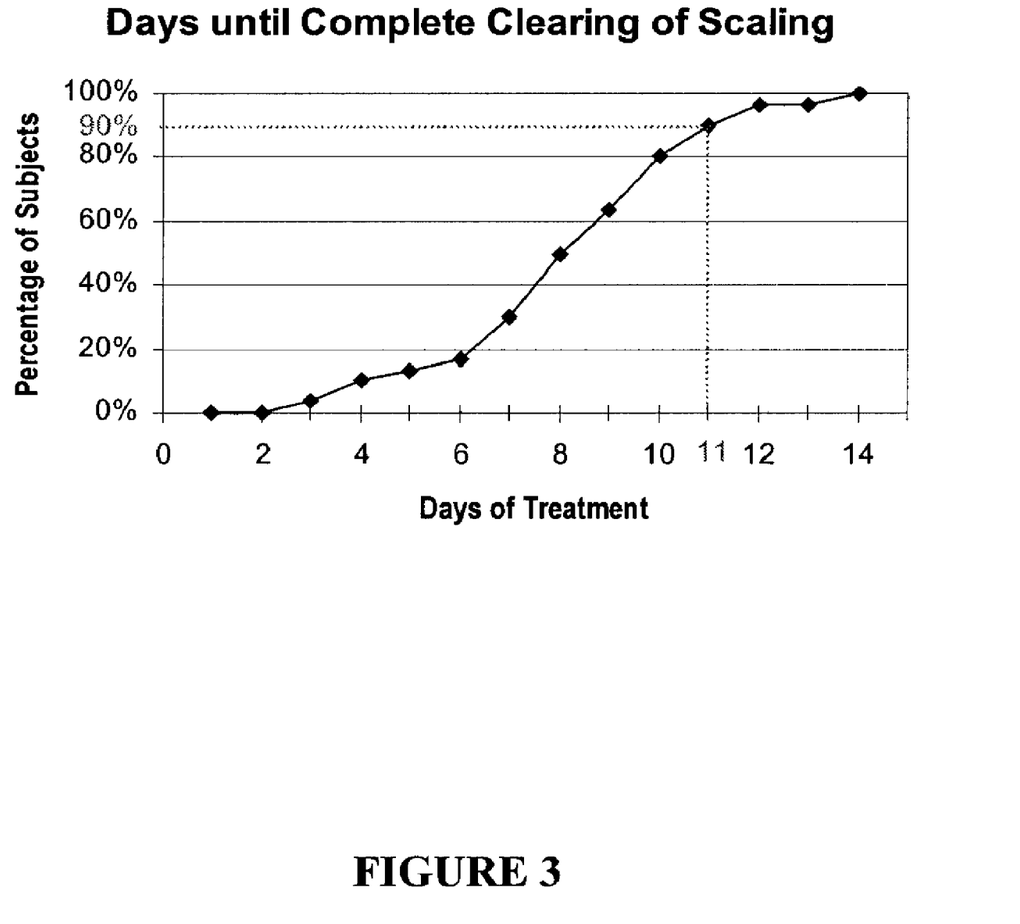
FIG. 3 is plot showing cumulative number of subjects reporting no clinical sign of scaling after number of days using the Dermesis Products. On day 11, 90% subjects reported complete clearing of scaling.

2) Results:

Based on basic scoring for scaling, all subjects had conditions that fell below the scale of 2, which is mild; fine, flaky scale predominated. The average score was 1.78 for 30 subjects. Age median was 32.5 years old. On safety evaluation, all subjects reported no adverse effects during the period of the study. The analysis of the Clinical Research Form has shown the time to reach no clinical sign of scaling for each subject as tabulated below and plotted in FIG. 3. It was observed that 90% subjects reported no clinical sign of scaling after 11 days of using the inventive toner and cream as instructed.

| Days of Treatment | Number of subjects | Cumulative No. Subjects | Percentage of Subjects |
|---|---|---|---|
| 1 | 0 | 0 | 0% |
| 2 | 0 | 0 | 0% |
| 3 | 1 | 1 | 3% |
| 4 | 2 | 3 | 10% |
| 5 | 1 | 4 | 13% |
| 6 | 1 | 5 | 17% |
| 7 | 4 | 9 | 30% |
| 8 | 6 | 15 | 50% |
| 9 | 4 | 19 | 63% |
| 10 | 5 | 24 | 80% |
| 11 | 3 | 27 | 90% |
| 12 | 2 | 29 | 97% |
| 13 | 0 | 29 | 97% |
| 14 | 1 | 30 | 100% |
| Total | 30 | | |

3) Conclusion

The study demonstrates the safety and efficacy of the inventive toner and cream to alleviate the symptoms of dry skin in minimal to mild cases. No adverse reaction was reported. 90% of subjects reported clearing of scaling after 11 days using the products.

What is claimed is:

1. A composition for skin care, comprising:
calcium chloride, magnesium chloride, and potassium bromide wherein the composition comprises about 0.01-8% w/w divalent calcium ions, and about 0.01-8% w/w divalent magnesium ions based on the total weight of the composition in a physiologically acceptable medium, and the weight ratio of calcium chloride to magnesium chloride ranges from about 2:1 to 1:3, and the weight ratio of divalent calcium chloride to potassium bromide ranges from about 6:1 to 1:5.

2. The composition according to claim 1, wherein the composition is an aqueous solution comprising at least 80% w/w water.

3. The composition according to claim 1, wherein the composition is an aqueous solution comprising at least 90% w/w water.

4. The composition according to claim 1, wherein the composition further comprises sodium monovalent cations, and the ratio of divalent calcium ions to monovalent cations ranges from 15:1 to 1:20.

5. The composition according to claim 1, wherein the composition further comprises sodium monovalent cations, and the ratio of divalent calcium ions to monovalent cations ranges from 4:1 to 1:3.

6. The composition according to claim 1, further comprising sodium ions.

7. The composition according to claim 6, wherein the sodium ions are provided by sodium chloride.

8. the composition according to claim 7, wherein the composition comprises calcium chloride and sodium chloride at a weight ratio ranging from 5:1 to 1:10.

9. The composition according to claim 7, wherein the composition comprises calcium chloride and sodium chloride at a weight ratio ranging from 2:1 to 1:3.

10. The composition according to claim 7, wherein the composition comprises calcium chloride and sodium chloride at a weight ratio of about 1:1.

11. The composition according to claim 10, wherein the composition further comprises potassium chloride and the weight ratio of calcium chloride to potassium chloride ranges from 10:1 to 1:5.

12. The composition according to claim 10, wherein the composition further comprises potassium chloride and the weight ratio of calcium chloride to potassium chloride is about 4:1.

13. The composition according to claim 12, wherein the weight ratio of calcium chloride to magnesium chloride ranges from about 2:1 to about 2:3.

14. The composition according to claim 12, wherein the weight ratio of calcium chloride to magnesium chloride is about 1:1.

15. The composition according to claim 13, wherein the weight ratio of calcium chloride to potassium bromide is about 4:1.

16. The composition according to claim 1, wherein the composition is in a form of emulsion.

17. The composition according to claim 16, wherein the composition further comprises an emulsifying surfactant at 2% to 30% by weight relative to the total weight of the composition.

18. The composition according to claim 17, wherein the emulsifying surfactant is a nonionic surfactant selected from the group consisting of: fatty acids, fatty alcohols, polyethoxylated stearyl or cetylstearyl alcohol, fatty acid esters of sucrose, alkylglucose esters, and a mixture thereof.

19. The composition according to claim 17, wherein the emulsifying surfactant is an anionic surfactant selected from the group consisting of: $C_{16}$-$C_{30}$ fatty acids neutralized with amines, aqueous ammonia or alkaline salts, and mixtures thereof.

20. The composition according to claim 16, wherein the amount of divalent calcium ion is about 0.1-0.3%.

21. The composition according to claim 16, further comprising: a sterol compound.

22. The composition according to claim 21, wherein the sterol compound is cholesterol or phytosterol.

23. The composition according to claim 16, further comprising: amino acids in an amount of 0.002-6% w/w based on the total weight of the composition.

24. The composition according to claim 16, further comprising: soluble collagen in an amount of 0.01-10% based on the total weight of the composition.

25. The composition according to claim 1, wherein the composition is in the form of a lotion, a gel, a water-in-oil emulsion, an oil-in-water emulsion, a triple emulsion, nanocapsules, liposomes, nanoemulsions, or oleosomes.

26. The composition according to claim 1, wherein the composition is storage-stable.

27. The composition according to claim 1, wherein the composition is in the form of a care cream, a milk, tonic, a cleansing or make-up-removing product, a mask, an erasing product, an exfoliant, a sunscreen product, a foundation, a tinted cream, or a lipstick.

28. The composition according to claim 1, wherein the composition in a form of aqueous-or hydro-gel.

29. The composition according to claim 28, wherein the composition further comprises a thickening agent.

30. The composition according to claim 29, wherein the thickening agent is selected from the group consisting of carbomers, cellulose base materials, gums, algin, agar, pectins, carrageenan, gelatin, mineral or modified mineral thickeners, polyethylene glycol, polyalcohols, and polyacrylamide.

31. The composition according to claim 28, wherein the amount of divalent calcium ions is about 0.05-0.8%.

32. A method for treating an undesirable skin condition of a mammal selected from the group consisting of adverse signs of aging of the skin, a dull complexion, skin or hair pigmentation disorders, and skin dryness, or a pathological skin condition of a mammal selected from the group consisting of acne vulgaris, blackheads or polymorphes, acne seniles, sunlight and medicinal or professional acne, comprising:

topically applying to the skin of the mammal a skin care composition of claim 1 comprising about 0.01-8% w/w divalent calcium ions or divalent magnesium ions based on the total weight of the composition in a physiologically acceptable medium for such period of time as required to elicit the desired cosmetic/therapeutic response.

33. The method according to claim 32, wherein the composition is in the form of aqueous solution comprising at least 90% of water and further comprises sodium monovalent cations, and the ratio of divalent calcium ions to monovalent cations ranges from 5:1 to 1:3 by weight.

34. The method according to claim 33, further comprising:

topically applying an emulsion comprising at least 70% of water and divalent calcium cations and monovalent cations at a ratio ranging from 8:1 to 1:2 by weight:.

35. The method according to claim 34, wherein the calcium ions are provided by calcium chloride; and monovalent cations are sodium chloride or potassium ions provided by sodium chloride, potassium chloride or potassium bromide.

36. The method according to claim 32, further comprising:

topically applying a cleansing composition comprising by weight at least 50% of water, about 0.01-1% of divalent calcium ions and a fatty film forming agent.

37. The method according to claim 36, wherein the fatty film forming agent is selected from the group consisting of decyl oleate, lauramide DEA, and glyceryl sterate.

38. The method according to claim 32, wherein the undesirable skin condition is selected from the group consisting of hyperseborrhoea, hyperseborrhoea-related imperfections, sensitive skin, dandruff, natural hair loss, and baldness.

39. The method according to claim 32, wherein the pathological skin condition is selected from the group consisting of, rosacea, extensive and/or severe forms of psoriasis, ichtyosis, Darier illness, palmoplantary keratodermies, leucoplasies, lichen plan, all benign dermatologic proliferations, rheumatoid psoriases, pruritus; erythams, atopic dermatitis, contact dermatitis, contact eczema, lichen planus, prurigo, urticaria, pruriginous toxidermia, and hyperkeratosis.

* * * * *